(12) United States Patent
Syrjälä et al.

(10) Patent No.: US 11,931,191 B2
(45) Date of Patent: Mar. 19, 2024

(54) CT IMAGING APPARATUS

(71) Applicant: PLANMECA OY, Helsinki (FI)

(72) Inventors: Tommi Syrjälä, Helsinki (FI); Timo Jokinen, Helsinki (FI); Timo Elonen, Helsinki (FI)

( * ) Notice: Subject to any disclaimer, the term of this patent is extended or adjusted under 35 U.S.C. 154(b) by 242 days.

(21) Appl. No.: 17/616,037

(22) PCT Filed: Jun. 1, 2020

(86) PCT No.: PCT/FI2020/050373
§ 371 (c)(1),
(2) Date: Dec. 2, 2021

(87) PCT Pub. No.: WO2020/245501
PCT Pub. Date: Dec. 10, 2020

(65) Prior Publication Data
US 2022/0296179 A1    Sep. 22, 2022

(30) Foreign Application Priority Data

Jun. 3, 2019  (FI) ..................... 20190042
Jul. 5, 2019  (FI) ..................... 20190054

(51) Int. Cl.
*A61B 6/03*    (2006.01)
*A61B 5/00*    (2006.01)
(Continued)

(52) U.S. Cl.
CPC ............ *A61B 6/035* (2013.01); *A61B 5/0088* (2013.01); *A61B 6/0407* (2013.01); *A61B 6/0442* (2013.01); *A61B 6/0487* (2020.08); *A61B 6/08* (2013.01); *A61B 6/14* (2013.01); *A61B 6/145* (2013.01); *A61B 6/4085* (2013.01);
(Continued)

(58) Field of Classification Search
CPC ..... A61B 6/035; A61B 5/0088; A61B 6/0407; A61B 6/0442; A61B 6/0487; A61B 6/08; A61B 6/14; A61B 6/145; A61B 6/4085; A61B 6/4452; A61B 6/4476; A61B 6/54; A61B 6/587; A61B 6/588; A61B 6/032; A61B 6/4435; A61B 6/04; A61B 6/4458; A61B 6/4429; A61G 15/02; A61G 2210/50; A61G 7/005; A61G 13/04; A61G 13/02
See application file for complete search history.

(56) References Cited

U.S. PATENT DOCUMENTS

2012/0324648 A1    12/2012  Amano
2018/0177473 A1    6/2018   Gregerson et al.
(Continued)

OTHER PUBLICATIONS

International Search Report for PCT/FI2020/050373, dated Sep. 21, 2020, 3 pages.

*Primary Examiner* — Kiho Kim
(74) *Attorney, Agent, or Firm* — Lippes Mathias LLP

(57) ABSTRACT

The invention relates, in particular, to structures of a dental and medical cone beam computed tomography (CBCT) apparatus. The basic construction of the apparatus includes two elongated frame parts (11, 21) out of which the first frame part (11) is arranged to support X-ray imaging means (14, 15) and wherein the frame parts (11, 21) are mechanically connected to each other via an articulated construction (22) so as to allow for tilting of the first frame part (11) supporting the X-ray imaging means (14, 15) with respect to the second frame part (21).

19 Claims, 8 Drawing Sheets

(51) Int. Cl.
*A61B 6/00* (2006.01)
*A61B 6/04* (2006.01)
*A61B 6/08* (2006.01)
*A61B 6/14* (2006.01)
*A61G 15/02* (2006.01)

(52) U.S. Cl.
CPC .......... *A61B 6/4452* (2013.01); *A61B 6/4476* (2013.01); *A61B 6/54* (2013.01); *A61B 6/587* (2013.01); *A61G 15/02* (2013.01); *A61B 6/588* (2013.01)

(56) References Cited

U.S. PATENT DOCUMENTS

2018/0177479 A1* 6/2018 Sato ........................ A61B 6/032
2018/0199901 A1  7/2018 Schraven

* cited by examiner

CT IMAGING APPARATUS

FIELD OF THE INVENTION

The invention relates to computed tomography imaging apparatus. In particular, features of an apparatus according to the invention are applicable for use in the context of dental and medical cone beam computed tomography (CBCT) imaging apparatus.

BACKGROUND OF THE INVENTION

Computed tomography (CT) is a kind of X-ray imaging in which a volume to be imaged is irradiated from different directions and, from the image information thus acquired, a desired two- or three-dimensional image can be reconstructed.

Traditional CT apparatus are large and massive, and they are typically mounted on a floor. A patient is positioned for imaging within an examination opening of the apparatus, typically on a horizontally extending and laterally movable examination platform.

Since development of cone beam computed tomography (CBCT) technology in which, for one, slower rotational speeds of the imaging means are used, apparatus of less weight than that of the more traditional CT apparatus have been developed. Among the CBCT apparatus, there are also e.g. ones which are not floor mounted but constructed to be mobile. Also, constructions comprising a vertically extending frame and a horizontally extending support for the imaging means have been designed.

Considering medical x-ray imaging apparatus in general, there are the kinds with no patient support construction in the apparatus itself at all, while those comprising a patient support construction are typically designed in view of imaging either a standing patient, a sitting patient or a lying patient.

BRIEF DESCRIPTION OF THE INVENTION

The object of the invention and of its preferable embodiments is a CT apparatus, especially a CBCT apparatus, applicable for versatile use and enabling imaging various parts of an anatomy in various ways. The characteristic features of the invention are defined in claim 1.

BRIEF DESCRIPTION OF THE FIGURES

The invention is now described in more detail in reference to its preferable embodiments and the attached drawings, of which.

DETAILED DESCRIPTION OF THE INVENTION

Figure 1:
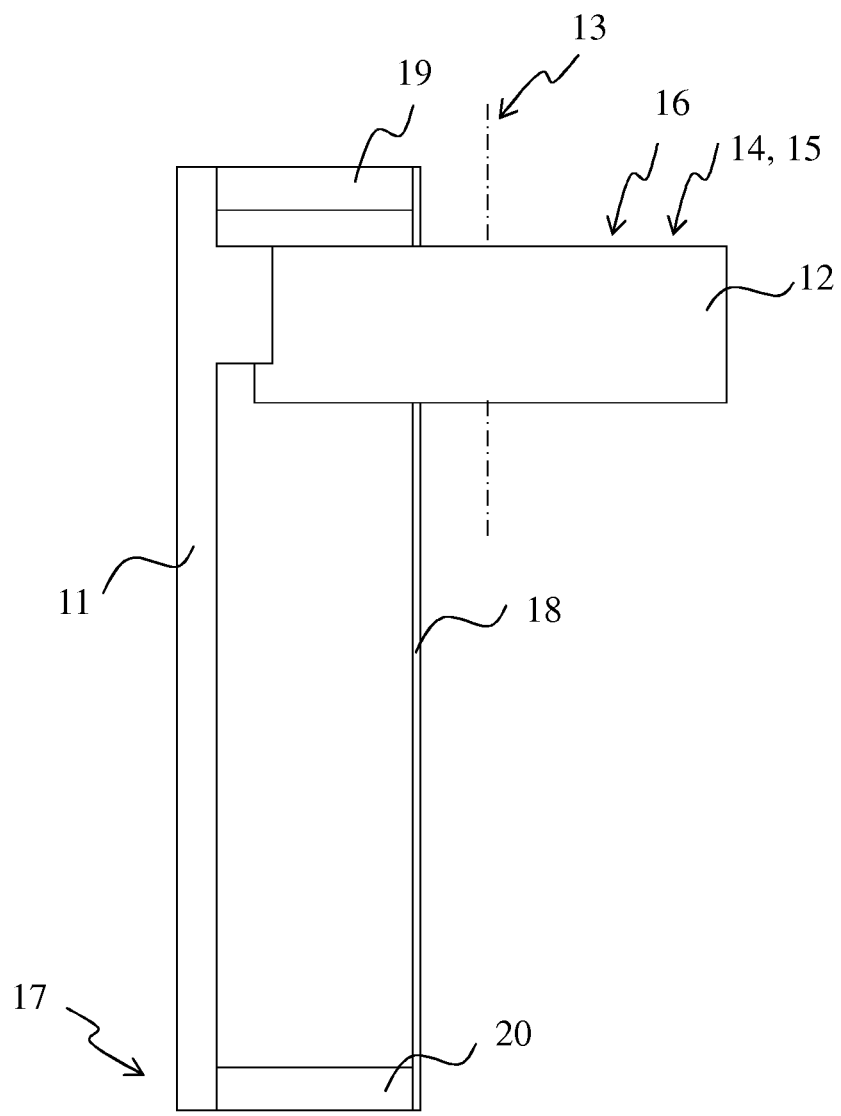
FIG. 1 is a schematic general side view showing certain components, as an example, of a part of an apparatus according to an embodiment of the invention.

FIG. 1 shows a schematic general side view of certain components of one embodiment, as an example, of a part of an apparatus according to the invention. The dental or medical CT imaging apparatus of FIG. 1 comprises an elongated frame part 11 extending in a first direction and having a first end and a second end. From this elongated frame part 11 extends in a second direction, which is substantially orthogonal to the first direction, a support construction 12 which supports an X-ray source 14 and an image detector 15 yet which as such are not visible in FIG. 1. The X-ray source 14 and the image detector 15, which together form X-ray imaging means 14, 15, may be mounted to the support construction 12 essentially opposite to each other yet in embodiments, their mutual position may also be arranged to be adjustable.

FIG. 1 further shows a patient support 18 which is a structure mechanically connected to the elongated frame part 11 and extending substantially in parallel with the elongated frame part 11. In the embodiment of FIG. 1, the patient support 18 is essentially of the same length as the elongated frame part 11.

According to one aspect, for example, the length of the elongated frame part 11 is of the order of 240 cm.

According one aspect, for example, the length of the elongated frame part 11 is between 220 cm and 260 cm.

According one aspect, for example, the length of the patient support 18 is 80-90% of the length of elongated frame part 11.

According to one aspect, for example, the patient support 18 has a longer dimension in a first direction and a shorter dimension in a second direction orthogonal to the first direction.

According to one aspect, for example, the patient support 18 is at least in the first direction at least for its prevailing part radiolucent.

According to one aspect, for example, the radiolucent part of the patient support 18 is of essentially the same length as the elongated frame part 11.

According to one aspect, for example, the patient support 18 comprises at least at either of its ends in the first direction a section which is not radiolucent.

According one aspect, for example, the length of the radiolucent part of the patient support 18 in the first direction is 80-90% of the length of the elongated frame part 11.

According to one aspect, for example, the support construction 12 supporting the X-ray imaging means 14, 15 is a circular gantry having a central axis 13. The gantry may partially encircle or completely house the X-ray imaging means 14, 15.

According to one aspect not directly visible in FIG. 1, for example, the apparatus comprises a driving mechanism 16 arranged to drive the X-ray imaging means 14, 15 about a rotation axis. This rotation axis may coincide with the central axis 13 of the support construction 12 in form of the gantry and it may be a physical axis, or a virtual rotation axis as in the case of FIG. 1.

According to one aspect, for example, the central axis 13 of the gantry coincides the center of rotation/the rotation axis of the X-ray imaging means 14, 15 when they are driven along a curved path.

According to one aspect, the rotation axis is an instantaneous (virtual) rotation axis and the location of the instantaneous rotation axis in relation to the central axis 13 can be arranged to be changed.

According to one aspect, at least either of the components the ray source 14 and the image detector 15 is arranged to be laterally movable from a location exactly opposite to the other component.

According to one aspect, the structure 12 supporting the X-ray imaging means 14, 15 comprises a gantry having a central axis and the structures of apparatus allows for at least either of: laterally moving the X-ray source 14 between positions at which a central ray it generates coincides with the central axis of the gantry and a position at which the central ray it generates does not coincide with the central axis of the gantry; laterally moving the image detector 15 between positions at which a vector which is normal to the detector surface at the center of the image detector 15 coincides the central axis of the gantry and a position at which the vector which is normal to the detector surface at the center of the image detector 15 does not coincide the central axis of the gantry. The lateral moving of the X-ray imaging means 14, 15 may include moving the X-ray imaging means 14, 15 to a position at which they face each other while the central ray the X-ray source 14 generates does not coincide the central axis of the gantry and the vector which is normal to the detector surface at the center of the image detector 15 does not coincide the central axis of the gantry.

According to another aspect, another driving mechanism 17 is arranged to the apparatus to enable moving the support construction 12 back and forth in a direction which is substantially parallel with the direction in which the elongated frame part 11 extends. According to one aspect, that driving mechanism 17 may be arranged to move the support construction 12 along or alongside the elongated frame part 11.

Figure 2A:
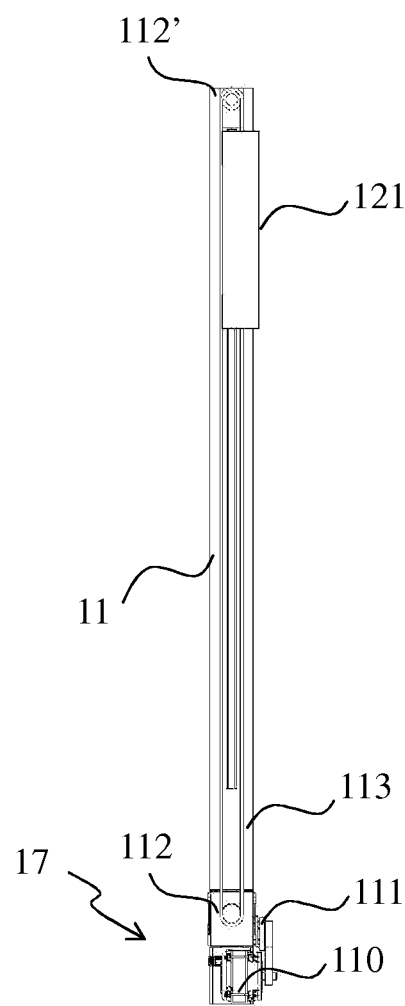
FIGS. 2a and 2b show structural details applicable for use in the context of an elongated frame of the apparatus of FIG. 1.
Figure 2B:
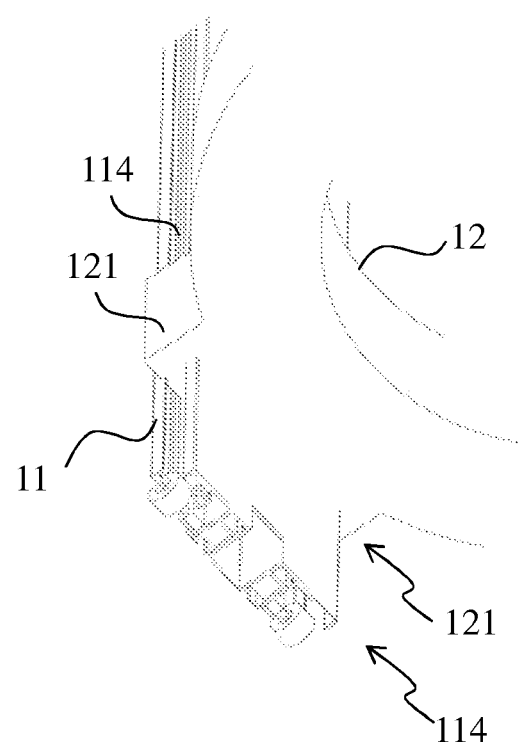

In the example according to FIG. 2a, the driving mechanism 17 of the support construction 12 discussed above comprises a motor 110 and a gearing 111 arranged to rotate a pulley 112. In the construction shown as one embodiment in FIG. 2a, while the motor 110 and the pulley 112 are located at the proximity of the second end of the elongated frame part 11 there is also another pulley 112' at the proximity of the first end of the elongated frame part 11 and around the pulleys 112, 112' goes a belt 113, or a correspondingly functioning component like a chain. This mechanism is then functionally connected to the support construction 12 to drive it along the elongated frame part 11, such as shown as an example in FIG. 2b where grooves 114 are arranged to the elongated frame part 11 and, to the support construction 12, projecting parts 121 which are fitted to slide along the grooves 114. In an embodiment, to minimize friction, roller type linear guide ways are used in which case the motion is rather rolling than sliding.

According to one aspect not shown in any of the FIGS., for example, the driving mechanism to drive the support construction 12 comprises a motor arranged to the support construction 12 itself.

Regardless of the details of the construction of the driving mechanism 17 to drive the support construction 12 along or alongside the elongated frame part 11, in one embodiment the construction of the apparatus allows for driving the support construction 12 essentially the whole length between the first and second ends of the elongated frame part 11.

According to yet another aspect and as shown is FIG. 1, the apparatus comprises a connection construction 19, 20 which connects the patient support 18 to the elongated frame part 11.

Figure 3A:
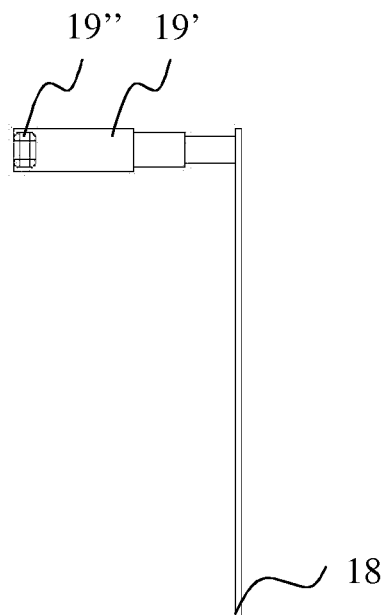
FIG. 3a shows as an example some details of a patient support construction applicable for use in an apparatus as the one shown in FIG. 1.

According to another aspect, an example of which is shown is FIG. 3a, the apparatus comprises a connection construction 19, 20 which mechanically connects the patient support 18 to the elongated frame part 11.

The connection construction 19, 20 may comprise a patient support adjustment mechanism 19', 20' configured to enable displacing the patient support 18 closer and further away from the elongated frame part 11.

According to another aspect, a driving mechanism 19'', 20'' is arranged in functional connection with the patient support adjustment mechanism 19', 20'.

According to another aspect, the patient support adjustment mechanism 19', 20' may comprise a first adjustment mechanism 19' arranged together with its driving mechanism 19'' comprised in the driving mechanism 19'', 20'' substantially at the first end of the elongated frame part 11, and a second adjustment mechanism 20' arranged together with its driving mechanism 20'' comprised in the driving mechanism 19'', 20'' substantially at the second end of the elongated frame part 11.

According to one aspect, for example, the patient support adjustment mechanisms 19', 20' is arranged in functional connection with the control system of the apparatus and the control system is configured to control the driving mechanism 19'', 20'' of the adjustment mechanism 19', 20'.

According to one aspect, for example, the control system is configured to control the connection construction 19, 20 comprising the first adjustment mechanism 19' with its driving mechanism 19'', arranged substantially at the first end of the elongated frame part 11, and the second adjustment mechanism 20' with its driving mechanism 20'', arranged substantially at the second end of the elongated frame part 11, to keep at the first and second ends of the elongated frame part 11 an identical distance between the elongated frame part 11 and the patient support 18 when adjusting the distance between the two.

According to another aspect, the distance between the ends of the elongated frame part 11 and the patient support 18 can be adjusted to be different. According to one aspect, the first and second adjustment mechanisms 19', 20' are arranged to be controlled independently.

Figure 3B:
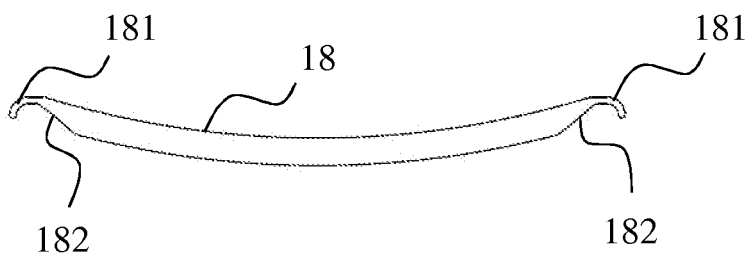
FIG. 3b shows an example of a cross section of the patient support construction applicable for use in an apparatus as the one shown in FIG. 1.

According to one aspect, as shown in FIG. 3b, considering the above-discussed first direction of the patient support construction 18, its cross section as for its prevailing part is curved so as to better support a patient against the concave surface of the patient support construction 18.

According to one aspect, as shown in FIG. 3b, at the edges 181 of that cross section of the patient support construction 18 the shape of the cross section turns into being curved in the opposite direction.

According to one other aspect and as further shown in FIG. 3b, near the edges of the above-discussed cross section of the patient support construction 18 and on the side opposite to the for its prevailing part concave surface is arranged a holding structure 182. The holding structure 182 may be e.g. an elongated handle or an attachment structure to receive a strap designed to extent on or over the concave side of the patient support construction 18, to be used to provide further support to the patient and thus to help keeping still during an imaging exposure.

Figure 4:
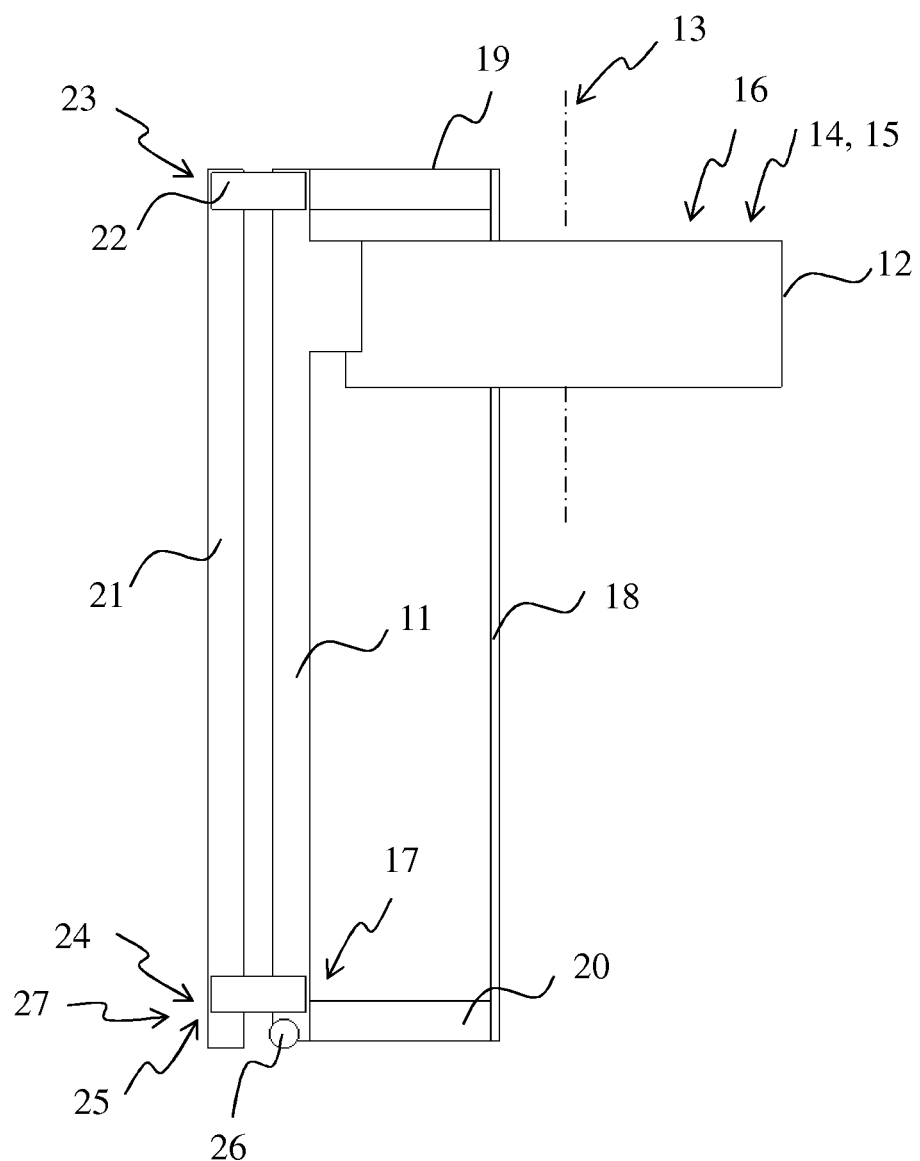
FIG. 4 is a schematic general side view showing certain components of an embodiment, as an example, of an apparatus according to the invention.

Turning to FIG. 4 which shows, as a schematic general side view, certain components of an embodiment, as an example, of an apparatus according to the invention in which, in addition to what can be referred to as a first elongated frame part 11 discussed above, there is a second elongated frame part 21 mechanically connected to the first elongated frame part 11 of essentially the same length as the first elongated frame part 11.

According to one aspect and still referring to FIG. 4, at the proximity of the first end of the first elongated frame parts 11, 12 is arranged an articulated connection construction 22 to mechanically connect the first and second elongated frame parts 11, 21, to allow for tilting of the first elongated frame part 11 about at least one tilt axis in relation to the second elongated frame part 21. The at least one tilt axis is orthogonal to both the abovementioned first and second directions in which the elongated frame part 11 and the support construction 12 extend. Or, in other words, the tilt axis may be an axis which is orthogonal to the direction in which the first and second elongated frame parts 11, 21 extend as well as to direction in which the support construction 12 for the X-ray imaging assembly 14, 15 extends— perpendicularly from the first longitudinally extending frame part 11.

In the embodiments shown in the FIGS. and discussed in more detail in this application, the at least one tilt axis is horizontal. This is not to be understood that the tilt axis needs to be horizontal.

According to another aspect, on the side of the second elongated frame part 21, a mounting structure 23 not directly visible in FIG. 4 is arranged in connection with the articulated connection construction 22. The mounting structure 23 is arranged movable along or alongside the second elongated frame part 21.

According to another aspect, for example, at the proximity of the second end of the second elongated frame part 21 is arranged a locking mechanism 24 configured to enable connecting and disconnecting the first and second elongated frame parts 11, 21. Particularly, a locking mechanism 24 may be arranged at the proximity of the second end of the first and second elongated frame parts 11, 21, the locking mechanism being configured to enable connecting together and disconnecting the first and second elongated frame parts 11, 21 at the proximity of the second ends of the first and second elongated frame parts 11, 21.

When the second elongated frame part 21 is mounted stable and the locking mechanism 24 is not connecting the first and second elongated frame parts 11, 21, the second end of the first elongated frame part 11 is free to move laterally while the articulated connection 22 between the frame parts 11, 21 allows for turning of the first elongated frame part 11 about the horizontal tilt axis at the proximity of the first end of the first elongated frame part 11. In case of a vertical starting position, such movably arranged mounting structure as discussed above allows for descending and ascending of the first end of the first elongated frame part 11.

Figure 5:
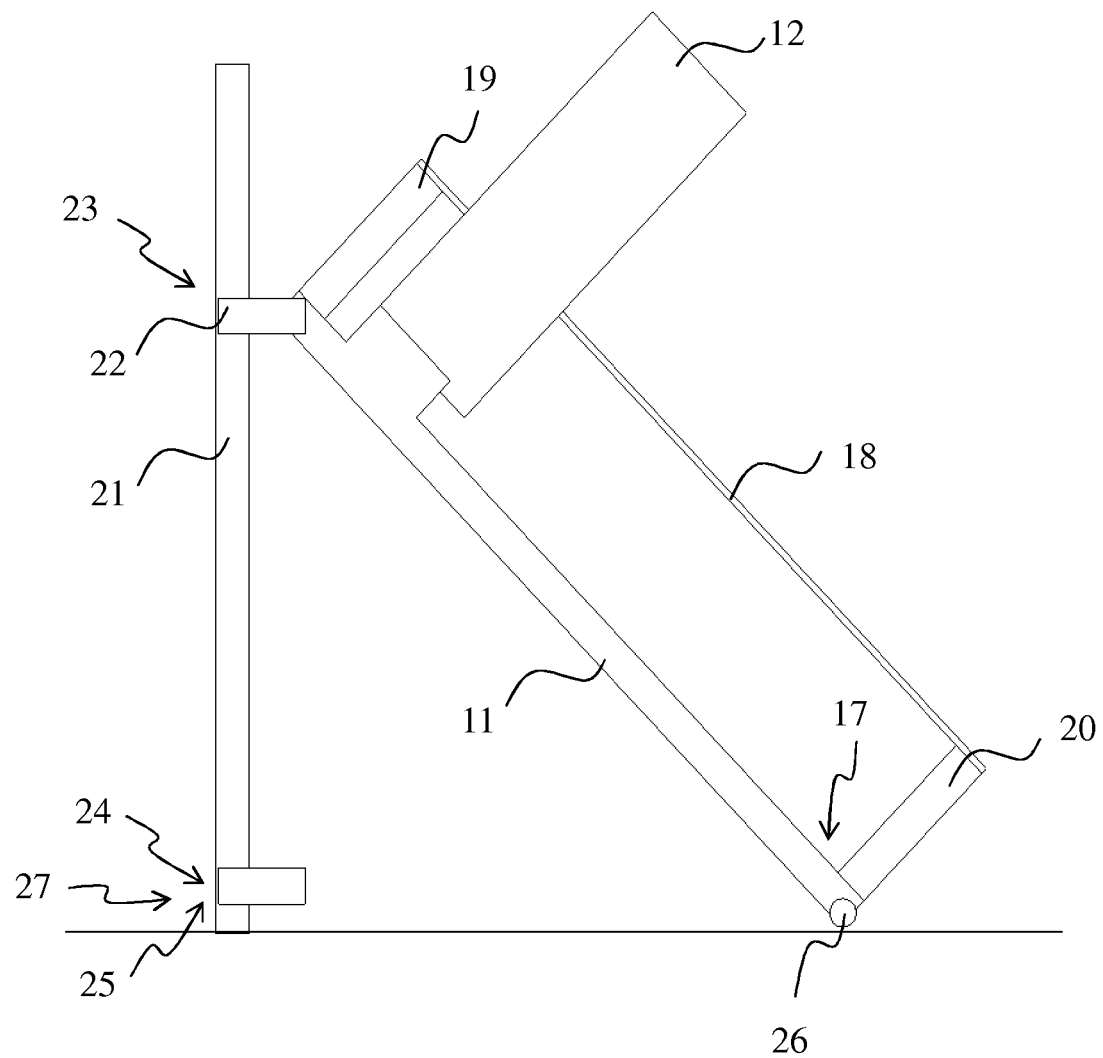
FIG. 5 is a schematic general side view of the apparatus of FIG. 4 showing certain components of the construction as driven at an inclined position.

FIG. 5 shows the apparatus according to FIG. 4 at a stage where the first end of the first elongated frame part 11 has moved downwards and the second end of the first elongated frame part 11 has moved horizontally on a surface. The apparatus may be configured to allow for descending of the first end of the first elongated frame part 11 all the way to the proximity of the second end of the second elongated frame part 21.

According to yet another aspect, not directly visible in FIGS. 4 and 5, in functional connection with the second elongated frame part 21 is arranged a driving mechanism 27 to drive the mounting structure 23 along or alongside the second elongated frame part 21. When being in mechanical connection with the first elongated frame part 11, at the proximity of the first end of it, the driving mechanism 27 can move the first end of the first elongated frame part 11 in a direction in which the second elongated frame part 21 extends.

The driving mechanism 27 to drive the mounting structure 23 may be a construction similar with the driving mechanism 17 driving the support construction 12 of the X-ray imaging means 14, 15 along or alongside the first elongated frame part 11.

According to one aspect, the driving mechanism 27 to drive the mounting structure 23 comprises a chain drive.

To describe some of the features discussed above in other words, in an embodiment in mechanical connection with the articulated connection construction 22, on the side of the second elongated frame part 21, is arranged a mounting structure 23 which is arranged movable along or alongside the second elongated frame part 21, such construction thereby providing a degree of freedom of movement along or alongside the second frame part 21 for the articulated connection construction 23 and for the first end of the first elongated frame part 11 mechanically connected to the articulated connection construction 23.

In an embodiment, the mounting structure 23 is arranged movable along or alongside the second elongated frame part 21 at least essentially a distance corresponding to the length of the first elongated frame part 11, and the articulated connection construction 22 is arranged to allow for tilting of the first elongated frame part 11 between orientations at which the first and second elongated frame parts 11, 21 extend essentially in parallel and at which the first and second elongated frame parts 11, 21 extend essential orthogonally.

According to yet another aspect, the locking mechanism 24 comprises a displacement mechanism 25 which is not directly visible in FIGS. discussed so far to move the second end of the first elongated frame part 11 a distance away from the second elongated frame part 21 when the locking mechanism 24 disconnects the first and second elongated frame parts 11, 21.

According to one aspect not shown in detail in the FIGS. discussed so far, the locking mechanism 24 comprises a motor driven arrangement with mating components on the side of a motorized structure and the first elongated frame part 11, respectively.

The locking mechanism 24 may further comprise a guiding construction configured to guide the second end of the first elongated frame part 11 straight on the locking mechanism 24 when the second end of the first elongated frame part 11 is moving towards the locking mechanism 24. Or, to put it in other words, when the second end of the first elongated frame part 11 moves towards and approaches the second end of the second elongated frame part 21.

According to yet another aspect and, as shown as an example in FIGS. 4 and 5, the first elongated frame part 11 comprises at the proximity of its second end at least one wheel or roller 26.

According to another aspect, instead of the wheel or roller, a structure designed to slide on a surface may be arranged at the second end of the first elongated frame part 11.

A more detailed embodiment concerning some of the features discussed above is presented in FIG. 6, which overall shows the second ends of the first and second elongated frame parts 11, 21 yet wherein the very end of the second end of the first elongated frame parts 11 is cut, partly completely cut and partly just one wall being cut so that what could be called a back wall 11' is still visible.

Figure 6:
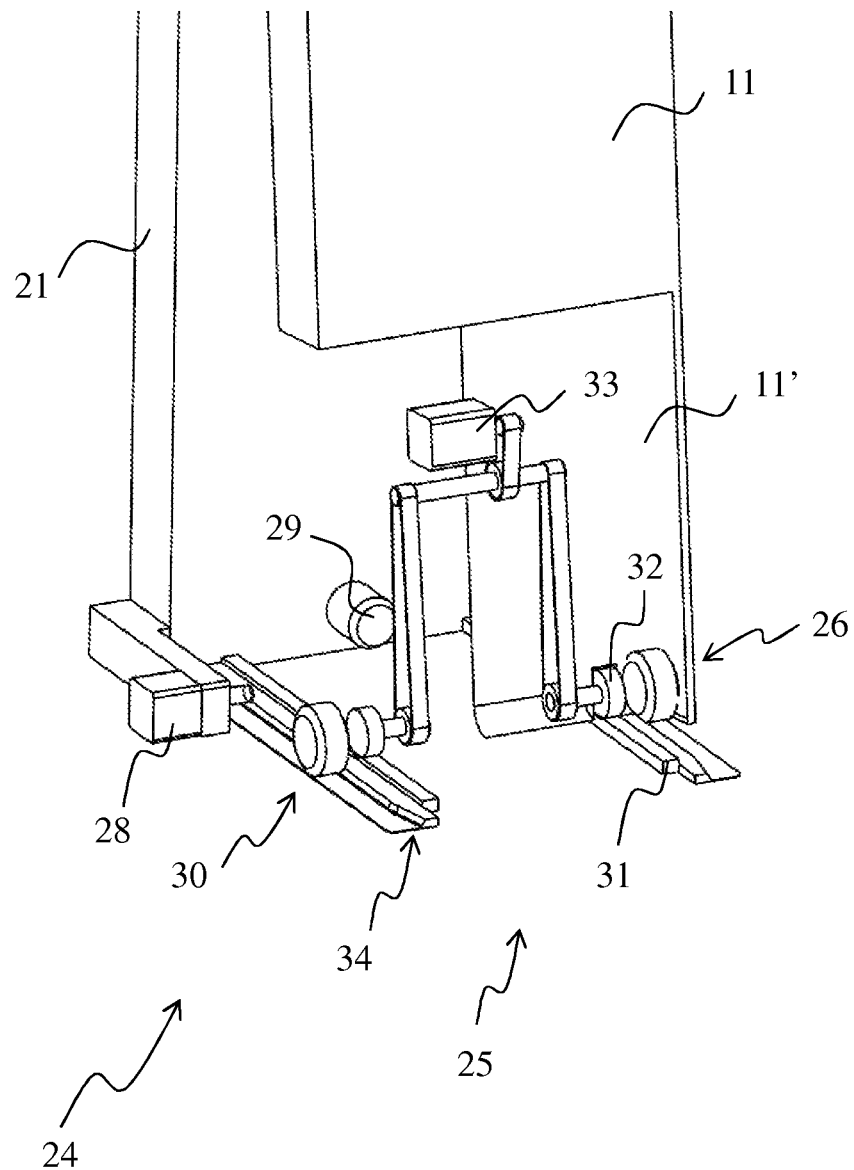
FIG. 6 shows components of an arrangement that can be used as a displacement and locking mechanism relating to the functionality of the apparatus as shown in FIG. 5.

The embodiment shown in FIG. 6 includes a structure in which the displacement mechanism 25 comprises two toothed bars 31 mounted at the proximity of the second end of the second elongated frame part 21, to extent essentially orthogonally to the direction at which the second elongated frame part 21 extends, and two toothed wheels 32 mounted at the proximity of the second end of the first elongated frame part 11. The toothed wheels 32 are configured compatible with the toothed bars 31. While two toothed bars and wheels are shown, the number of those could be just one, or more than two.

The embodiment shown in FIG. 6 further includes the displacement mechanism 25 comprising a displacing motor 33 arranged in functional connection with toothed wheels 32.

According to one embodiment, to operate the displacement mechanism 25, the control system of the apparatus may be configured to, when the first and second elongated frame parts 11, 21 extend essentially in parallel and as a response to a control signal to alter the mutual orientation of the first and second elongated frame parts 11, 21, first operate the displacement mechanism 25 to move the second end of the first elongated frame part 11 a distance away from the second end of the second elongated frame part 21 and, second, operate said third driving mechanism 27 to drive the mounting structure 23 along or alongside the second elongated frame part 21 towards the second end of the second elongated frame part 21, so as to move the second end of the first elongated frame part 11 a further distance away from the second end of the second elongated frame part 21.

The locking mechanism 24 shown in FIG. 6 further comprises a sensing element 29 configured to detect when the second end of the first elongated frame part 11, when moving towards the second end of the second elongated frame part 21, has reached a predefined locking position.

The locking mechanism 24 shown in FIG. 6 further comprises a locking actuator 28 and the control system of the apparatus may be configured to, as a response to a control signal from the sensing element 29 that the second end of the first elongated frame part 11 when moving towards the second end of the second elongated frame part 21 has reached a predefined locking position, send a control signal to the locking actuator 28 to lock the second end of the first elongated frame part 11 at said predefined locking position.

The guiding construction according the embodiment of FIG. 6 comprises two guide rails 30 mounted from their first end at the proximity of the second end of the second elongated frame part 21 and extending essentially orthogonally to the direction at which the second elongated frame part 21 extends, to form two guide passages. While two guide rails 30 are shown in FIG. 6, the number of rails could be something else as well—yet, using just one rail it may be difficult to form a passage truly having a guiding function.

While shown in FIG. 6 is the first elongated frame part 11 to comprise at the proximity of its second end two wheels, or rollers 26, at a first distance from each other, and the guiding construction to comprise two guide rails 30 to form two guide passages essentially at the same first distance from each other, the guide rails 30 further comprise at their second ends a beveling so as to make a distance between the guide passages smaller at that end of the passages than the first distance. Such construction aids in guiding the second end of the first elongated frame part 11 to find a designed passage to move towards the second elongated frame part 21.

Figure 7:
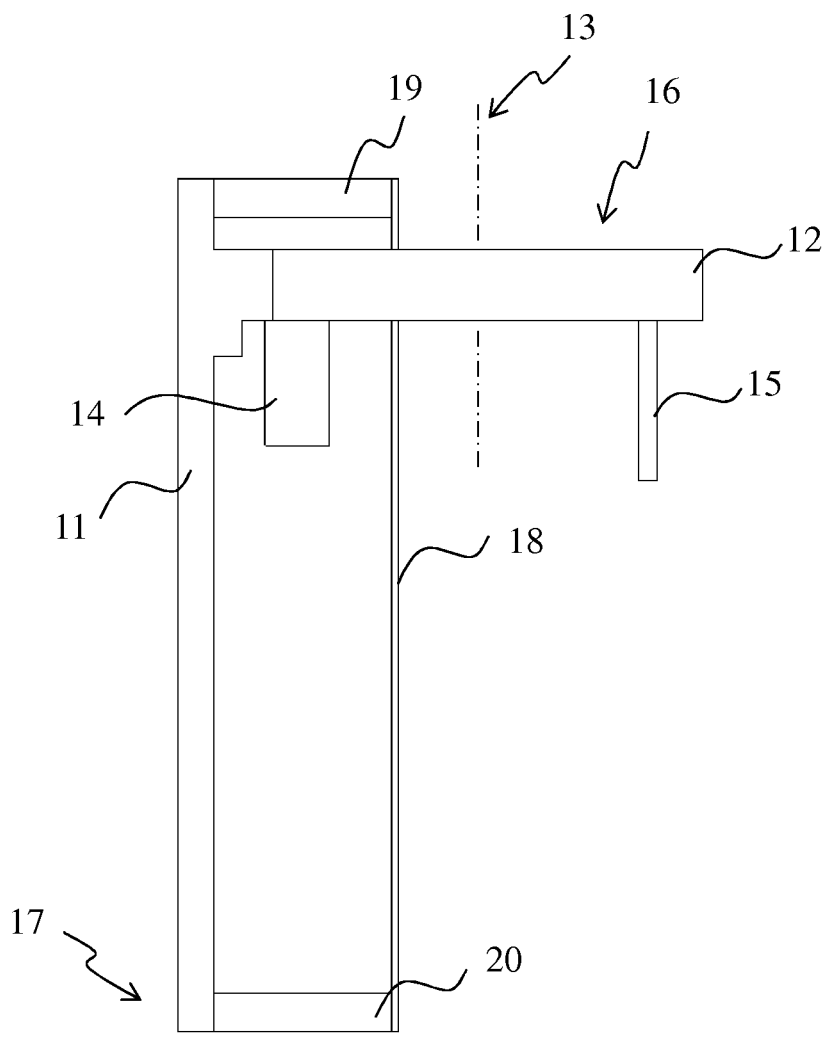
FIG. 7 is a schematic general side view showing another embodiment of certain components, as an example, of a part of an apparatus according to the invention.

According to one aspect, for example and as shown in FIG. 7, support construction 12 for the imaging means 15, 16 in a form of a gantry basically does not completely encircle the imaging means 14, 15 but functions primarily or solely as a support structure for holding the imaging means 14, 15, and structures arranged to the gantry to drive the imaging means 14, 15 about an axis. This kind of solution enables realizing the gantry as less heavy and as providing better access to the volume between the imaging means 14, 15, both physically and considering an area from where one may have a clear line of sight at that volume.

Figure 8:
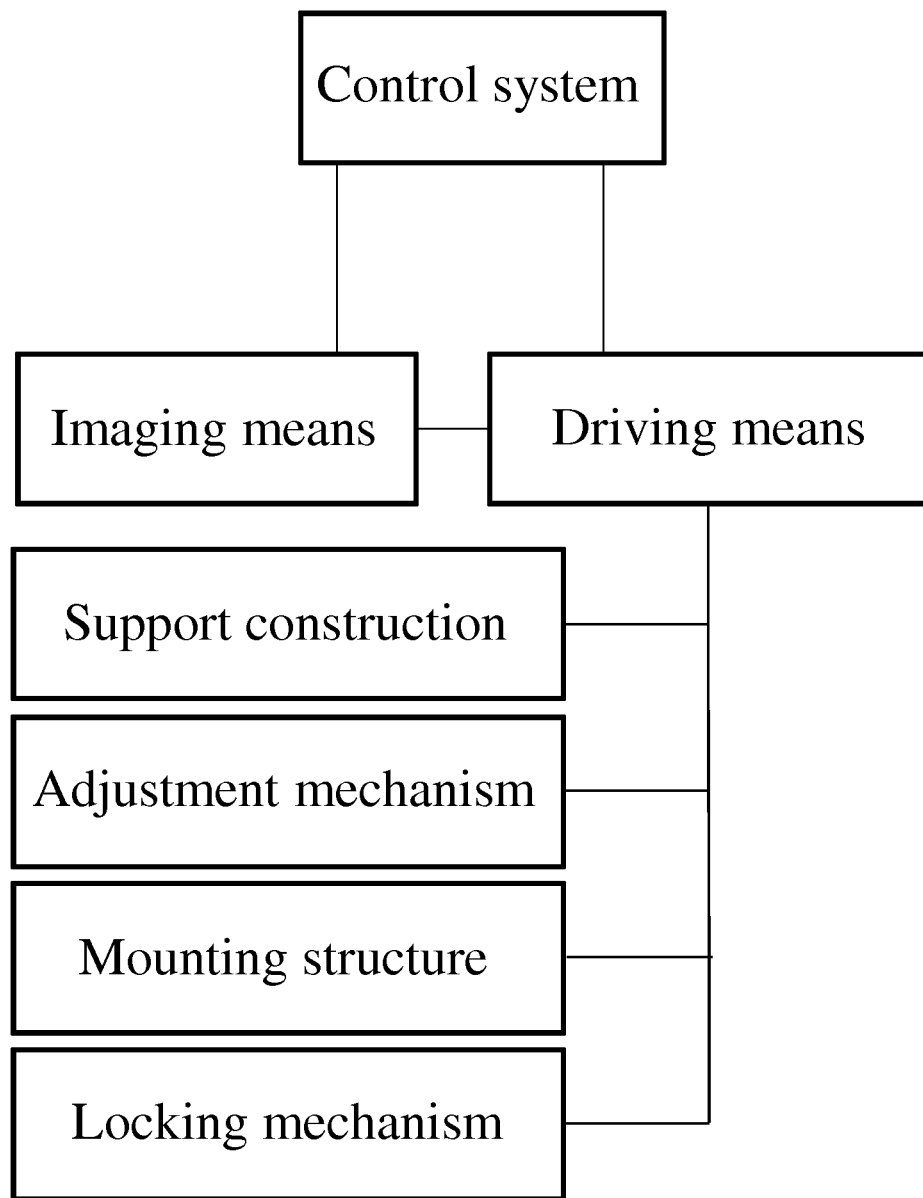
FIG. 8 is a block diagram showing an example of components which a control system of an apparatus according to the invention may be configured to control.

FIG. 8 shows as a block diagram an example of components of a control system applicable for use in an apparatus according to this disclosure. In various embodiments, not all those features are necessarily present in a control system of the apparatus. The control system according to FIG. 8 is configured to enable controlling, first of all, operation of the X-ray source and the image detector. Components controlling operation of the X-ray source and the image detector can include components physically arranged to the Xx-ray source and/or the image detector and/or elsewhere in the apparatus.

The control system of FIG. 8 further controls various driving means of the apparatus, such as those moving the imaging means supported by the support construction, the support construction itself and the adjustment mechanism of the patient support. The control system may also control e.g. driving of the mounting structure as discussed above. Further, in case of the apparatus comprising a motorized locking mechanism to connect and disconnect the first and second elongated frame parts, the control system may also control driving means of the locking mechanism, like the displacing motor and the locking actuator discussed above. Overall, the control system may be arranged to control all the above-discussed operations or any portion thereof. Inputs to the control system may be provided by the remote control. The structures and functionalities discussed above offer various possibilities for positioning and imaging a patient.

The invention claimed is:

1. A dental or medical CT imaging apparatus, comprising:
    a first elongated frame part extending in a first direction and comprising a first end and a second end;
    a support construction extending from the first elongated frame part in a second direction substantially orthogonal to the first direction;
    an X-ray source and an image detector mounted to the support construction which together form an X-ray imaging means;
    a first driving mechanism arranged to move the imaging means, about an axis;
    a second driving mechanism arranged to move the support construction in a direction substantially parallel with the first direction in which the first elongated frame part extends;
    a patient support;
    a control system;

characterized in that the apparatus comprises a second elongated frame part comprising a first end and a second end of essentially the same length as the first elongated frame part, wherein at the proximity of the first end of the first elongated frame parts, is arranged an articulated connection construction to mechanically connect the first and second elongated frame parts, to allow for tilting of the first elongated frame part about at least one tilt axis in relation to the second elongated frame part, the at least one tilt axis being orthogonal to both said first and second directions.

2. An apparatus according to claim 1, characterized in that in mechanical connection with the articulated connection construction, on the side of the second elongated frame part, is arranged a mounting structure which is arranged movable along or alongside the second elongated frame part, thereby providing for the articulated connection construction and for the first end of the first elongated frame part mechanically connected to the articulated connection construction a degree of freedom of movement along or alongside the second frame part.

3. An apparatus according to claim 2, characterized in that the mounting structure is arranged movable along or alongside the second elongated frame part at least essentially a distance corresponding to the length of the first elongated frame part, and the articulated connection construction is arranged to allow for tilting of the first elongated frame part between orientations at which the first and second elongated frame parts, extend essentially in parallel and at which the first and second elongated frame parts, extend essential orthogonally.

4. An apparatus according to claim 2, characterized in that the apparatus comprises a third driving mechanism to drive the mounting structure along or alongside the second elongated frame part.

5. An apparatus according to claim 1, characterized in that the patient support is a structure mechanically connected to the first elongated frame part and extending substantially in parallel with the first elongated frame part in said first direction.

6. An apparatus according to claim 5, characterized in that the patient support is essentially of the same length as the first elongated frame part.

7. An apparatus according to claim 6, characterized in that the patient support is at least in said first direction at least for its prevailing part radiolucent.

8. An apparatus according to claim 1, characterized in that at the proximity of the second end of the first and second elongated frame parts, is arranged a locking mechanism configured to enable connecting together and disconnecting the first and second elongated frame parts, at the proximity of the second ends of the first and second elongated frame parts.

9. An apparatus according to claim 8, characterized in that the locking mechanism comprises a displacement mechanism configured to move the second end of the first elongated frame part a distance away from the second end of the second elongated frame part when the locking mechanism disconnects the first and second elongated frame parts.

10. An apparatus according to claim 9, characterized in that the displacement mechanism comprises at least one toothed bar mounted at the proximity of the second end of the second elongated frame part, to extent essentially orthogonally to the direction at which the second elongated frame part extends, and at least one toothed wheel mounted at the proximity of the second end of the first elongated frame part and configured compatible with said toothed bar.

11. An apparatus according to claim 10, characterized in that the displacement mechanism comprises a displacing motor arranged in functional connection with said at least one toothed wheel.

12. An apparatus according to claim 9, characterized in that the control system is configured to, when the first and second elongated frame parts, extend essentially in parallel and as a response to a control signal to alter the mutual orientation of the first and second elongated frame parts, first operate the displacement mechanism to move the second end of the first elongated frame part a distance away from the second end of the second elongated frame part and, second, operate said third driving mechanism to drive the mounting structure along or alongside the second elongated frame part towards the second end of the second elongated frame part, so as to move the second end of the first elongated frame part a further distance away from the second end of the second elongated frame part.

13. An apparatus according claim 8, characterized in that the locking mechanism comprises a sensing element configured to detect when the second end of the first elongated frame part, when moving towards the second end of the second elongated frame part, has reached a predefined locking position.

14. An apparatus according claim 13, characterized in that the locking mechanism comprises a locking actuator, and the control system is configured to, as a response to a control signal from the sensing element that the second end of the first elongated frame part when moving towards the second end of the second elongated frame part has reached the predefined locking position, send a control signal to the locking actuator to lock the second end of the first elongated frame part at said predefined locking position.

15. An apparatus according to claim 8, characterized in that the locking mechanism comprises a guiding construction configured to guide the second end of the first elongated frame part straight on the locking mechanism when the second end of the first elongated frame part moves towards and approaches the second end of the second elongated frame part.

16. An apparatus according to claim 15, characterized in that the guiding construction comprises at least one guide rail mounted from its first end at the proximity of the second end of the second elongated frame part and extending essentially orthogonally to the direction at which the second elongated frame part extends, to form at least one guide passage.

17. An apparatus according to claim 1, characterized in that the first elongated frame part comprises at the proximity of its second end at least one wheel or roller, or a structure designed to slide on a surface.

18. An apparatus according to claim 17, characterized in that the first elongated frame part comprises at the proximity of its second end two wheels or rollers at a first distance from each other and the guiding construction comprises at least two guide rails to form two guide passages essentially at the same first distance from each other, wherein the at least two guide rails comprise at their second ends a beveling so as to make a distance between the guide passages smaller at that end of the passages than the first distance.

19. An apparatus according to claim 1, characterized in that driving of the support construction in a direction substantially parallel with said first direction is arranged possible for essentially the whole length between the first and second ends of the first elongated frame part.

* * * * *